United States Patent [19]

Porat et al.

[11] Patent Number: 4,815,460
[45] Date of Patent: Mar. 28, 1989

[54] GRIPPER TEETH FOR MEDICAL INSTRUMENTS

[76] Inventors: Michael Porat; Amir Porat, both of 2 Kufman St., P.O. Box 50355, Tel Aviv - 61500, Israel

[21] Appl. No.: 191,787

[22] Filed: May 3, 1988

Related U.S. Application Data

[63] Continuation of Ser. No. 892,336, Jul. 31, 1986, abandoned, which is a continuation of Ser. No. 704,331, Feb. 22, 1985, abandoned.

[30] Foreign Application Priority Data

Sep. 26, 1984 [IL] Israel ............................ 73079

[51] Int. Cl.⁴ .................................. A61B 17/00
[52] U.S. Cl. ..................... 128/303 R; 128/321; 128/354
[58] Field of Search ............ 128/303 R, 321, 354; 24/455, 459; 294/99.2, 106

[56] References Cited

U.S. PATENT DOCUMENTS

3,140,715  7/1964  Whitton, Jr. et al. ............. 128/321
3,879,813  4/1975  Shadwell ............................ 24/455

Primary Examiner—Robert Peshock
Assistant Examiner—J. Hakomaki
Attorney, Agent, or Firm—Abelman Frayne Rezac & Schwab

[57] ABSTRACT

Gripper teeth on one part of a medical instrument, such as forceps, are symmetrically arranged on opposite sides of a median line, the teeth at one side of the median line being staggered by one half pitch relative to the teeth at the opposite side of the median line, whereby, the gripper teeth can interfit with mutually presented identically formed gripper teeth on another part of the medical instrument without the need to stagger the respective parts of the medical instrument, and, without the need to form the respective parts as non-identical parts.

2 Claims, 3 Drawing Sheets

GRIPPER TEETH FOR MEDICAL INSTRUMENTS

This application is a continuation of application Ser. No. 892,336, filed July 31, 1986, now abandoned, which is a continuation of Ser. No. 704,331, filed Feb. 22, 1985, now abandoned.

FIELD OF THE INVENTION

The present invention concerns gripper means on medical instruments such as forceps, clamps and the like.

BACKGROUND OF THE INVENTION

Forceps and the like medical instruments have been made of metal, the provision of the gripper means thereon being effected by special operating procedures such as milling, stamping or the like. Since this is a costly process, plastic forceps have come into use in which the gripper means can be cast or molded together with the entire instrument. However, for each instrument two separate molds have to be provided for the respective gripping members so that when an instrument is assembled from two parts, the gripper means will properly engage, one with the other.

SUMMARY OF THE INVENTION

It is the object of the present invention to provide a gripper means for medical instruments, which permits proper interengagement of two identical parts to make one instrument, thus eliminating the need to provide two separate molds.

The invention consists in gripper means on the gripper parts of medical instruments, comprising teeth which extend at the same angle at the two sides of an imaginary longitudinal median line of said part, the teeth at one side being staggered axially along the median line relative to those at the other. In this manner when assembling two parts of an instrument with the gripper means facing each other, the teeth on a side of the median line will interengage in the interstices between the teeth on the other part on the same side of the said median line.

It has been found that the gripping action of this arrangement is much more positive than that in any of the gripper means known up until now.

DESCRIPTION OF THE DRAWINGS

The invention is illustrated in the accompanying drawings showing a gripper part of a medical instrument according to the invention, and in which.

DESCRIPTION OF THE PRIOR ART

Figure 2:
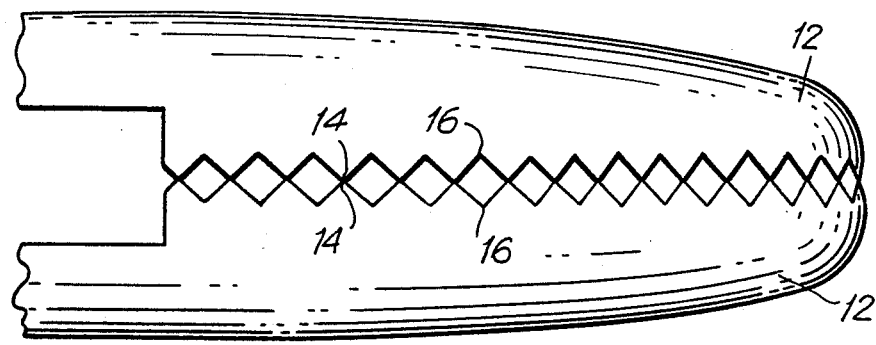
FIG. 2 is illustrative of the prior art, and illustrates the condition that arises when two identical gripping members are brought into engagement with each other.
Figure 3:
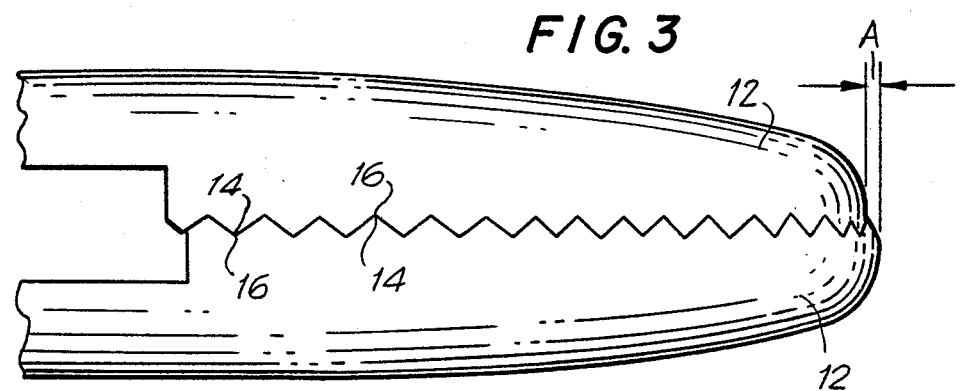
FIG. 3 also is illustrative of the prior art, and illustrates the positional adjustment that must be made in order to secure correct interengagement of the respective gripping members.

In order to provide for better understanding of the present invention, a discussion of the prior art is first made, as related to FIGS. 2 and 3 of the drawings, which are illustrative of a prior art gripper means construction, comprised of two identical cast or molded gripper means 12.

If the respective gripper means 12 are cast or molded from a single mold, such that they are truly identical one with the other, then, when the respective gripper means 12 are brought into engagement with each other in correct positional relationship, the crests 14 of the teeth of the respective gripper members 12 will come into point or line contact one with the other as illustrated in FIG. 2.

This condition is not desirable, in that it is injurious to human tissue, the inter-engaged crests 14 constituting points of extreme pressure which can actually cause cutting of the human tissue. This is particularly so in the event that one of the crests slips relatively to the opposite crest, in which event the crests will act in a shear-like manner, with further damage to the human tissue.

As will be readily apparent, the condition illustrated in FIG. 2 is to be avoided in order to minimize damage to the human tissue, it being preferable that the crests 14 of the respective gripping members 12 interfit with the valleys 16 of the oppositely presented gripping member.

This condition is illustrated in FIG. 3, which shows the crests 14 of the respective members 12 as being interfitted within the valleys 16 of the respective members 12.

However, this interfitting of the crests and valleys only can be accomplished in the event that one of the gripping members 12 is displaced relative to the opposite gripping member by a distance of one-half pitch of the gripping teeth, as indicated at A in FIG. 3.

Thus, according to the prior art, either one of the gripping members 12 must be displaced relative to the opposite gripping member by one half of the pitch of the teeth as illustrated in FIG. 3, if the teeth are to correctly interfit, or, two separate molds must be employed, one for molding the upper gripping member 12, and the other for molding the lower gripping member 12, the respective molds providing for the one-half pitch shift of the respective gripping teeth.

This problem is overcome in its entirety by the teachings of the present invention, in which correct interfitting of the teeth of the respective gripping members is obtained in the total absence of shifting one of the gripping members relative to the other, and, in the absence of a need to provide two separate molds as is required to provide interfitting of the teeth of the respective gripping members in the absence of shifting of one of the gripping members relative to the other.

A preferred embodiment of the present invention will now be discussed with reference to FIGS. 1, 4 and 5, each of which is illustrative of identical gripping members 12 which have been formed in a single mold, and, in which there is no requirement for shifting of one of the gripping members 12 relative to the other in order to obtain correct interengagement of the gripping teeth of the respective gripping members.

DESCRIPTION OF THE PREFERRED EMBODIMENT

The tip of an instrument 20, such as a forceps, is provided with teeth 23 and 24, which are arranged at the same angle on each side of the imaginary median line 22 of said instrument. The angle which the teeth make with said imaginary line may be of any degree, from an in line arrangement to an acute angle. The teeth 23 on one side of said line 22 are staggered with relation to the teeth 24 on the other side of said line 22 by exactly one half pitch relative to the teeth at the opposite side.

Thus, when two identical parts of a medical instrument cast or molded according to the invention from plastic or metal, or stamped from metal, are assembled, with one part facing the other, the crests of the teeth 24 of one part will be engaged in the valleys or interstices between the crests of the teeth 3 of the other part, thereby imparting a tight gripping means to the instrument in the absence of any cutting action of the interengaged teeth.

Figure 1:
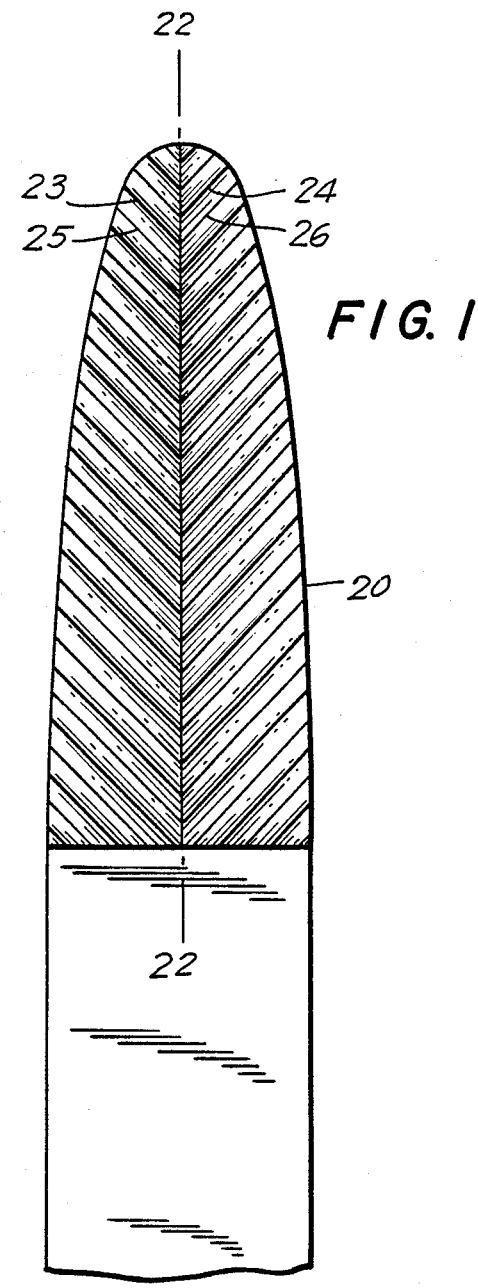
FIG. 1 is a front elevation of one of the two gripping members of a medical forceps.

In FIG. 1, the crests 23 and 24 of the respective teeth are indicated in bold lines, and, the valleys or interstices between the respective teeth 23 and 24 is indicated in fient lines 25 and 26.

Thus, as will be apparent from a consideration of FIG. 1, each crest 23 of the teeth at one side of the median line 22 merges at the median line 22 into a valley or interstice 26 of the teeth at the opposite side of the median line 22. Conversely, the crest 24 of each of the teeth at the other side of the median line 22 merges at the median line into a valley or interstice 25 of the teeth at the opposite side of the median line.

Figure 4:
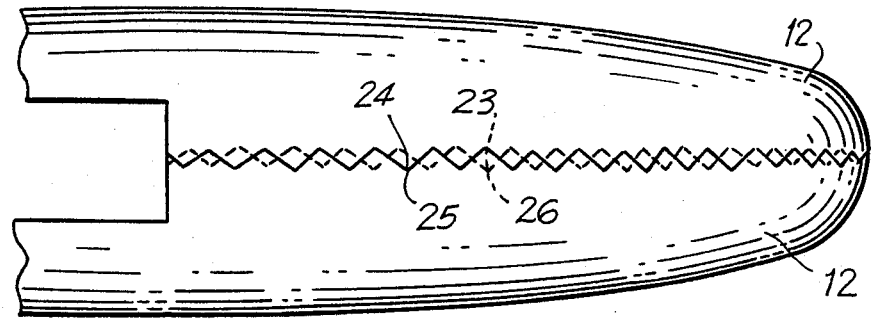
FIG. 4 is illustrative of the present invention, and shows that the gripping members of the invention can properly interengage, without the need to adjust their positional relationship; and, FIG. 5 is a perspective view of the respective gripping members of the pair prior to their interengagement.

This is further illustrated in FIG. 4, from which it will be seen that, without staggering of the respective gripping members 12, the crests of the gripping teeth 24 in the top gripping member 12 are received directly within the valleys or interstices 25 of the lower gripping member 12, which is identical with the upper gripping member 12, but which has been reversed by rotating it through 180 degrees. In an identical manner, the crests 23 at the opposite side of the upper gripping member 12 are received in the valleys or interstices 26 at the opposite side of the lower gripping member 12. This relationship will now be described with reference to FIG. 5, which is illustrative of a pair of identical gripping members in the process of being assembled one to the other without staggering of one of the gripping members relative to the other.

Figure 5:
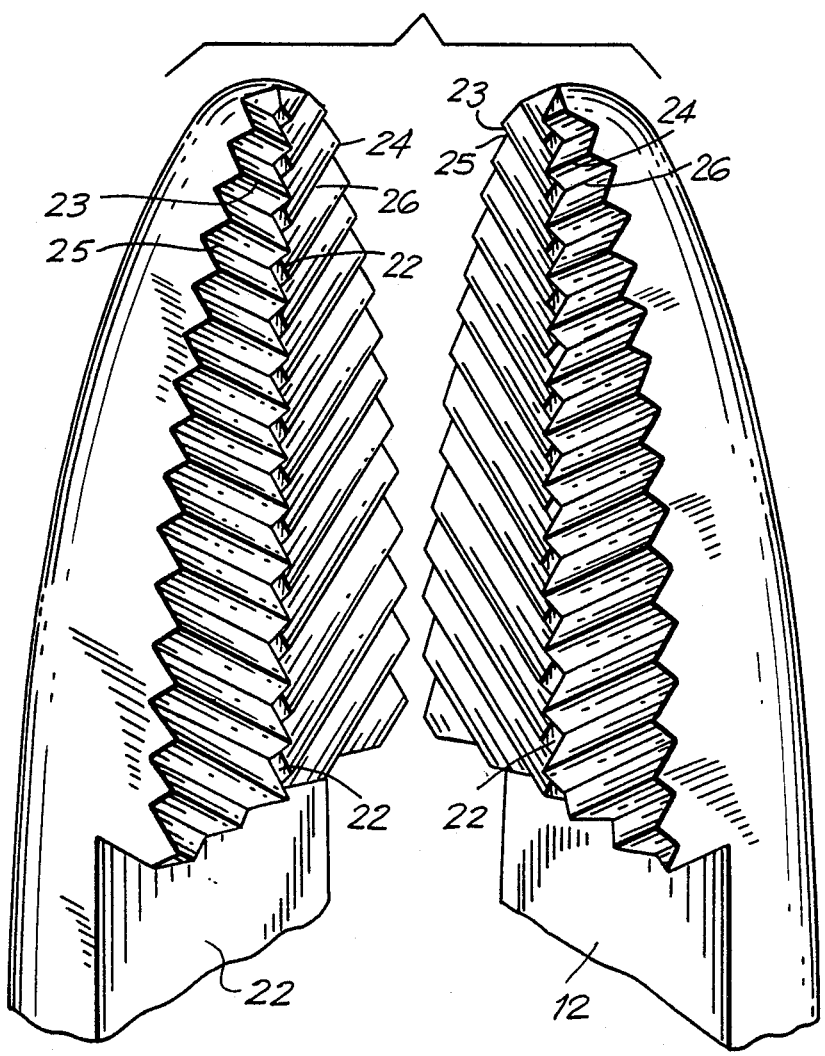

In correspondence with FIG. 1, the gripping member at the left hand side of FIG. 5 shows the gripping teeth 23 being positioned at the left-hand side of that gripping member, and the gripping teeth 24 as positioned at the right-hand side of that member.

If now the griping member 12 at the left-hand side of FIG. 5 is rotated through 180 degrees to bring it into the position of the gripping member 12 illustrated at the right-hand side of FIG. 5, then, it will be seen that the teeth 23 and 24 are positioned oppositely to the teeth 23 and 24 at the left-hand side of FIG. 5, as are the valleys or interstices 25 and 26.

Thus, having positioned a pair of identical gripping members in facing relationship one with the other, the respective gripping members 12 can be moved into engagement with each other as illustrated in FIG. 4, without any need for displacing one of the gripping members relative to the other by one-half pitch of the gripping teeth.

In this manner, the problems of cutting or excessive pressure points at the inter-engaged crests of the opposed teeth is eliminated without the requirement for offsetting the respective gripping members one from the other by one-half pitch of the teeth. Also, it will be seen that both of the gripping members 12 are identical in all respects one with the other thus permitting the respective gripping members to be formed in the same mold.

While the teeth of the gripping members of the present invention have been illustrative as being arranged at an angle to the median line 22, it will be appreciated that this angle either could be increased or decreased, or, that it could be reversed, or, that the teeth 23, 24, could in fact extend parallel one with the other, provided that the relationship is maintained that the teeth at one side of the median line 22 are staggered at one-half pitch relative to the teeth at the opposite side of the median line 22.

Further, the respective teeth 23, 24 do not necessarily need to be axially straight and continuous. They could be curved or sinusoidal throughout their respective lengths, and, if desired, could be provided with discontinuities throughout their lengths, provided that the condition is maintained that the teeth at one side of the median line 22 are a mirror-image of the teeth at the opposite side of the median line 22 as displaced by one-half pitch of the respective sets of teeth.

We claim:

1. A gripping portion of a medical instrument having opposed jaws, comprising:
   first and second teeth on each said jaw, said respective first and second teeth being arranged on opposite sides of an imaginary line bisecting the associated jaw;
   the improvement comprising said first teeth of each said jaw being arranged in staggered relation relative to said second teeth of the associated jaw by one-half pitch of the respective teeth, for them to be interfittable and meshable with the second and first teeth of an identical, oppositely presented jaw in the absence of axial displacement of one of said jaws relative to the other, and which includes:
   crests of said first teeth terminating at said imaginary line in corresponding valleys of said second teeth;
   valleys of said first teeth terminating at said imaginary line in corresponding crests of said second teeth;
   said first and second teeth being oriented relative to said imaginary line for them to be symmetrical about said imaginary line;
   whereby, upon presentation of one said jaw to an oppositely presented said jaw in longitudinally aligned relationship, said first teeth of said one jaw mesh and directly interfit with said second teeth of said oppositely presented jaw, and, said second teeth of said one jaw mesh and directly interfit with said first teeth of said oppositely presented jaw.

2. The gripping portion of a medical instrument of claim 1, in which said respective first and second teeth are arranged in herringbone formation.

* * * * *